United States Patent
Shiku et al.

(10) Patent No.: US 6,656,481 B1
(45) Date of Patent: Dec. 2, 2003

(54) VACCINAL PREPARATIONS

(75) Inventors: Hiroshi Shiku, Mie (JP); Junzo Sunamoto, Shiga (JP); Hideo Nakamura, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/147,773

(22) PCT Filed: Sep. 5, 1997

(86) PCT No.: PCT/JP97/03123

§ 371 (c)(1),
(2), (4) Date: Jul. 3, 1999

(87) PCT Pub. No.: WO98/09650

PCT Pub. Date: Mar. 12, 1998

(30) Foreign Application Priority Data

Sep. 6, 1996 (JP) .............................................. 8-236937

(51) Int. Cl.⁷ .............................................. A61K 45/00
(52) U.S. Cl. ................................ 424/278.1; 424/185.1; 424/204.1; 424/277.1; 424/283.1
(58) Field of Search ........................... 424/185.1, 277.1, 424/204.1, 278.1, 283.1

(56) References Cited

U.S. PATENT DOCUMENTS

| | | |
|---|---|---|
| 4,189,471 A | 2/1980 | Ponpipom et al. |
| 4,229,441 A | 10/1980 | Bugianesi et al. |
| 4,259,324 A | 3/1981 | Ponpipom et al. |
| 5,736,146 A | 4/1998 | Cohen et al. |
| 6,015,567 A | 1/2000 | Hudziak et al. |

FOREIGN PATENT DOCUMENTS

| | | |
|---|---|---|
| EP | 12083 | 6/1980 |
| EP | 23865 | 2/1981 |
| EP | 34835 | 9/1981 |
| EP | 640347 | 3/1995 |
| JP | 61-69801 | 4/1986 |
| JP | 63319046 | 12/1988 |
| JP | 3-292301 | 12/1991 |
| JP | 7-97333 | 4/1995 |
| JP | 7-206903 | 8/1995 |
| WO | 90/14357 | 11/1990 |
| WO | 92/04887 | 2/1992 |
| WO | 94/20070 | 9/1994 |
| WO | 00/20563 | 4/2000 |

OTHER PUBLICATIONS

Bocchia et al. Antitumor vaccination: where we stand. Haematologica 85:1172–1206, 2000.*

Cox et al., Adjuvants—a classification and review of their modes of action. Vaccine 15(3):248–256, 1997.*

Takahashi et al., Nature, vol. 344,873–875, 1990.

Newman et al., J. Immunol., vol. 148, No. 8,2357–2362, 1992.

Ray Chaudhuri et al., Proc. Natl. Acad. Sci., USA, vol. 89, pp. 8308–8312, 1992.

Akiyoshi et al., Macromolecules, vol. 26, No. 12, pp. 3062–3068, 1993.

Akiyoshi et al., Proc. Japan Acad., vol. 71, Ser. B, pp. 15–19 (1995).

Nishikawa et al., Macromolecules, vol. 26, No. 26, pp. 7654–7659, 1994.

Coussens et al., Science, vol. 230, pp. 1132–139, 1985.

Deleo et al., J. Exp. Med., vol. 146, pp. 720–734, 1977.

English Language Patent Abstracts of –JP–7–97333.

English Language Patent Abstracts of –JP–7–206903.

English language excerpt of –JP–61–69801.

English language excerpt of –JP–3–292301.

English language excerpt of –JP–63–319046.

Nishikawa et al., *J. Am. Chem. Soc.*, vol. 118, pp. 6110–6115 (1996).

Nestle et al., *Nature Medicine*, vol. 4, No. 3, pp. 328–332 (1998).

Mukherji et al., *Proc. Natl. Acad. Sci. USA*, vol. 92, pp. 8078–8082 (1995).

Hu et al., *Cancer Research*, vol. 56, pp. 2479–2483 (1996).

L. Wang et al., *Int. J. Oncol.*, 14(4), 695, 1999.

*Byotai Seiri* (Pathophysiology), vol. 6, No. 10, pp. 771–780 (1987). (No translation).

M. Mauk et al., *Proc. Natl. Acad. Sci. USA*, vol. 77, No. 8, pp. 4430–4434 (1980).

* cited by examiner

*Primary Examiner*—Donna C. Wortman
(74) *Attorney, Agent, or Firm*—Greenblum & Bernstein, P.L.C.

(57) ABSTRACT

Vaccinal preparations comprising an antigen such as tumor-associated antigens and viral antigens, together with a hydrophobized polysaccharide as adjuvant, e.g., hydrophobized polysaccharides containing a saccharide unit whose primary hydroxyl group is represented by the following formula: $-O-(CH_2)_m CONH(CH_2)_n NH-CO-O-R$ wherein R represents an alkyl group or a sterol residue; m represents 0 or 1; and n represents an arbitrary positive integer, at a ratio of one to five units per 100 saccharide units that constitute the polysaccharide, preferably comprising an antigen encapsulated in microparticles of aggregated hydrophobized polysaccharide.

56 Claims, 4 Drawing Sheets

Fig.1

| Inoculated Cell | Inoculated Cell |
| CMS7HE | CMS7neo |

1. CHM — erbB2

2. CHM — CAB

3. CHP — erbB2

Fig.2

Inoculated Cell CMS7HE | Inoculated Cell CMS7neo

4. CHP — CAB 5. erbB2

6. CAB

7. NAIVE

Fig. 3

1. CHM − erbB2

2. CHM − CAB

3. CHP − erbB2

4. CHP − CAB

5. erbB2

6. CAB 7. naive

Target Cell:
- ■ CMS7HE
- ● CMS17HE
- □ CMS7neo
- ○ CMS17neo
- + CMS7 (Parent Strain)

Fig.4

SEQUENCE LISTING

<160> NUMBER OF SEQ ID NOS: 2

<210> SEQ ID NO 1
<211> LENGTH: 24
<212> TYPE: DNA
<213> ORGANISM: synthetic construct

<400> SEQUENCE: 1
agctgcagtg atcaccatgg agct                                              24

<210> SEQ ID NO 2
<211> LENGTH: 29
<212> TYPE: DNA
<213> ORGANISM: synthetic construct

<400> SEQUENCE: 2
tgaattctat gtgagacttc gaagctgca                                         29

VACCINAL PREPARATIONS

TECHNICAL FIELD

The present invention relates to a vaccinal preparation comprising an antigen and a hydrophobized polysaccharide. More specifically, it relates to a vaccinal preparation comprising antigens such as tumor-associated antigens and virus antigens, together with a hydrophobized polysaccharide which acts as an adjuvant, wherein the antigens and the hydrophobized polysaccharide form a complex. The vaccinal preparation of the present invention has, in particular, activating and inducing effects on cytotoxic T cells (abbreviated as "CTL" hereinafter in the specification) that are specific for the antigen, and therefore, the preparation is extremely useful as a vaccine for preventive and/or therapeutic treatment of cancers, viral diseases and autoimmune diseases.

BACKGROUND ART

CTLs have actions of specifically recognizing cancer cells or virus-infected cells through their T cell receptors or other, and destroying or damaging the cells. Their roles are important as a bio-defense mechanism against cancers or viruses. Recently, it has been revealed that T cell receptors of CTL do not directly recognize the specific antigen expressed on the surface of cancer cells or virus-infected cells. Instead, they recognize complexes including an MHC class I antigen, which is expressed on the surface of antigen-presenting cells, per se, such as macrophages, dendritic cells, cancer cells or virus-infected cells, together with an oligopeptide derived from the specific antigen bound to the MHC class I antigen ("CTL epitope" of the specific antigen).

It is considered that the complex of an MHC class I antigen/an oligopeptide derived from a specific antigen is formed by a processing as explained below. Antigenic proteins are synthesized in cytoplasm, and then some of the proteins are degraded into oligopeptides by intracellular protease complexes ("proteasome"). Some of the oligopeptides (consisting of 9–10 amino acid residues) are then transported from cytoplasm into the endoplasmic reticulum membrane by transporter proteins (TAP: transporter in antigen processing) that are present in the endoplasmic reticulum membrane, and oligopeptides having high affinity for the MHC class I antigen are preferentially bind to the MHC class I antigen and presented on the surfaces of the cells.

It has been attempted to develop vaccines that artificially can activate the CTL (CTL-activating vaccines) in order to provide a method of preventive and/or therapeutic treatment of cancers, viral diseases or autoimmune diseases by eliminating cancer cells, virus-infected cells or autoantigen-reactive lymphocytes. To achieve the aforementioned purpose, it is necessary to perform immunization of a living body with cancer cells or virus-infected cells, per se, which expresses specific antigens, or alternatively, to introduce the specific antigens or the oligopeotides derived therefrom into the processing machinery for the antigen presenting cells so that a complex with the MHC class I antigen can be expressed.

In order to develop such "CTL-activating vaccines", some attempts were made which include, for example, 1) a method comprising the step of transforming a gene encoding a specific antigenic protein by means of a viral vector; 2) a method comprising the step of introducing a specific antigenic protein having an appropriate molecular weight and several CTL epitopes into cytoplasm by means of a certain technique, and 3) a method comprising the step of binding an oligopeptide consisting of 9–10 amino acid residues as a potential CTL epitope directly to an MHC class I antigen of an antigen presenting cell.

Among them, method 1) is a so-called gene therapy, whose efficacy and safety have not yet been established. Efficacy obtained by using method 3) have been shown in animal studies; however, practical problems may arise for applications to humans. Since almost every patient has different kind of MHC class I antigens, it should be necessary to cover the diversity of CTL epitopes corresponding to the variety of antigens. In other words, it is necessary to elucidate amino acid sequential motifs of oligopeptides having high affinity for each kind of the MHC class I antigens, and to provide customized oligopeptides as medicaments that correspond to each of the MHC class I antigen. Therefore, the development of vaccines based upon this class will be extremely difficult.

As to the approach according to method 2), some successful examples are known and its efficacy and safety seem satisfactory. Therefore, the method has been expected as a most successful means to develop the CTL activating vaccines applicable to variety of patients. However, when a specific antigenic protein, per se as a polypeptide, is administered to a living body to activate specific CTLs, the protein is usually administered as a mixture with an adjuvant. For example, ISCOM (Takahashi et al., Nature, 344, 873–875, 1990), QS-21 (Newman et al., J. Immunol., 148, 2357–2362, 1992), mannan-coated liposomes (WO92/4887), AF (Raychaudhuri et al., Proc. Natl. Acad. Sci. USA, 89, 8308–8312, 1992) or other have been reported as such adjuvant.

It is known that polysaccharide/cholesterol derivatives can be used as polysaccharide coatings for liposomes [Japanese Patent Unexamined Publication (KOKAI) No. (Sho)61-69801/1986], or coatings for lipid emulsions [Japanese Patent Unexamined Publication (KOKAI) No. (Sho)63-319046/1988]. As explained above, it is also known that tumor-associated antigens or virus antigen/liposome complexes, coated with polysaccharides containing mannose, have inducing activity of CTL (WO92/4887).

However, all of the aforementioned products should be manufactured by a coating process using a polysaccharide/cholesterol derivative after a liposome formation or a lipid emulsification of an antigenic protein (an antigen). As for a complex consisting solely of a polysaccharide/cholesterol derivative and an antigenic protein (an antigen), anything has not been reported as to what effects can be specifically obtained by the complex.

As mentioned above, in order to activate specific CTLs by administering a kind of antigenic protein as a polypeptide, to human, it is necessary to use a certain adjuvant. However, no adjuvant has been available which achieves efficient immunization and safety, and can be readily prepared.

DESCRIPTION OF THE INVENTION

The inventors of the present invention conducted various studies to discover a substance which can be used as a simpler and more efficient adjuvant. As a result, they found that hydrophobized polysaccharides composed of naturally occurring polysaccharides modified with alkyl groups or cholesterol groups can encapsulate, quite readily and efficiently, tumor-associated antigenic proteins or virus antigenic proteins to form complexes without any need of phospholipids. They also found that specific CTLs were activated in animals administered with the complex and bio-defense reactions were induced. The present invention was achieved on the basis of these findings.

The present invention thus provides vaccinal preparations comprising a hydrophobized polysaccharide and an antigen, and vaccinal preparations comprising a complex of a hydrophobized polysaccharide and an antigen. According to preferred embodiments of the present invention, there are provided the aforementioned vaccinal preparations which contain an antigen encapsulated in microparticles comprising aggregated hydrophobized polysaccharides; and the aforementioned vaccinal preparation comprising the hydrophobized polysaccharide as an adjuvant. Those vaccinal preparations can be used for, for example, anti-cancer and anti-viral or autoimmune disease therapies.

According to preferred embodiments of the present invention, there are provided the aforementioned vaccinal preparations wherein the hydrophobized polysaccharide is a polysaccharide modified with an alkyl group or a sterol residue; the aforementioned vaccinal preparations wherein the hydrophobized polysaccharide is characterized to contain a saccharide unit, at a ratio of one to five per 100 saccharide units that constitute the polysaccharide, whose primary hydroxyl group is a group represented by the following formula (I):

—O—(CH$_2$)$_m$CONH(CH$_2$)$_n$NH—CO—O—R      (I)

wherein R represents an alkyl group or a sterol residue; m represents 0 or 1; and n represents an arbitrary positive integer; the aforementioned vaccinal preparations wherein the polysaccharide is pullulan or mannan; and the aforementioned vaccinal preparations wherein the sterol residue is cholesterol residue.

According to further preferred embodiments of the present invention, there are provided the aforementioned vaccinal preparations wherein the antigen is a protein which is presented as an oligopeptide by an MHC class I antigen and induces cytotoxic T-cells; the aforementioned vaccinal preparations wherein the antigen is ErbB-2 protein; and the aforementioned vaccinal preparations wherein the antigen is a tumor-associated antigen, a viral antigen, or an autoantigen-reactive T-cell receptor.

As another aspect of the present invention, there are provided methods for immunization which comprises the step of administering to a mammal the aforementioned vaccinal preparations; and the aforementioned methods which are used for inducing antigen-specific cytotoxic T-cells. As a further aspect of the present invention, adjuvants comprising a hydrophobized polysaccharide are provided. As a preferred embodiment of the aforementioned invention, the adjuvants are provided which are used for the formulation of a vaccinal preparation together with an antigen. There is also provided a use of a hydrophobized polysaccharide for the manufacture of the aforementioned vaccinal preparations.

BEST MODE FOR CARRYING OUT THE INVENTION

As used herein, the term "adjuvant" means a substance which is used together with an antigen to modify an immune response against the antigen, and the term includes those used generally for enhancing antibody production and cellular immunity, as well as those optionally used for changing immune response in its nature.

<1> Antigen

The antigens used according to the present invention are not particularly limited so long as they induce immunity. For example, polypeptides, polypeptide complexes, glycoproteins, nucleic acids and other may be used. The antigen may be a pathological target, per se, such as viruses or cancer cells, or a part thereof. Alternatively, the antigens may be those produced by pathological tissues such as neoplastic tissues and virus-infected cells. According to the present invention, antigenic proteins, in particular, those presented as oligopeptides by MHC class I antigens and inducing CTLs may preferably be used. The antigenic proteins are not limited so far that they contain one or more antigenic determinants, and their origin and purity are not particularly limited. However, for example, those produced by genetic recombinant techniques are preferred. Molecular weight of the antigenic proteins may generally be from about 500 to 100,000, preferably from about 2,000 to 100,000. More specifically, examples include oncogene products, ErbB-2 protein, ras p21 protein, tumor suppressor gene product p53 protein, virus derived protein, T cell receptors such as autoantigen-reactive (i.e., autoimmune disease-inducing) T cell receptors, and proteins containing a partial sequence thereof.

<2> Hydrophobized Polysaccharide

The hydrophobized polysaccharides or the microparticles comprising hydrophobized polysaccharide aggregates can be produced by known methods, for example, those described in Akiyoshi et al., Macromolecules, 6, pp.3062–3068, 1993; Akiyoshi et al., J. Proc. Japan. Acad., 71, 71B, p.15, 1995; Japanese Patent Unexamined Publication (KOKAI) Nos.(Sho)61-69801/1986, (Hei)3-292301/1991, (Hei)7-97333/1995 and other.

Polysaccharides constituting the hydrophobized polysaccharide are not particularly limited so long as they are polymers composed of saccharide residues linked by glycoside bonds. Examples of the saccharide residues constituting the polysaccharides include, for example, monosaccharides such as glucose, mannose, galactose, and fucose, and those derived from disaccharides, oligosaccharides and the like. The saccharide residues may be linked with 1,2-, 1,3-, 1,4- or 1,6-glycoside bond, and the bond may be either in α- or β-linkage. The polysaccharide may be linear or branched. Glucose residue is preferred as the saccharide residue. As the polysaccharide, naturally occurring or synthesized polysaccharides such as pullulan, dextran, amylose, amylopectin, mannan and the like, preferably mannan and pullulan may be used.

As the hydrophobic group, for example, mono-chain or bi-chain alkyl groups or sterol groups are preferably introduced at a ratio of 1 to 5 modifications per 100 monosaccharide units (5% by weight or less). However, the hydrophobic groups are not limited to those mentioned above, and those achieving high encapsulating ratio can be appropriately chosen depending on the molecular weight, isoelectric point and other of an antigen to be encapsulated. As the sterol residue, for example, cholesterol, stigmasterol, β-sitosterol, lanosterol, ergosterol residues and others can be used, and cholesterol residue can be preferably used as the sterol residue. As the alkyl group, those having 20 or less of carbon atoms, more preferably 10–18 carbon atoms can be used, and they may be linear or branched.

As the hydrophobized polysaccharide, a preferred example includes those containing a saccharide unit, at a ratio of one to five per 100 saccharide units that constitute the polysaccharide, whose primary hydroxyl group is represented by the following formula (I):

—O—(CH$_2$)$_m$CONH(CH$_2$)$_n$NH—CO—O—R    (I)

wherein R represents an alkyl group or a sterol residue; m represents 0 or 1; and n represents an arbitrary positive integer. As the alkyl group and the sterol residue, those mentioned above may preferably be used. The symbol "n" may preferably be from 1 to 8. As the hydrophobized polysaccharide, those formed by means of linkers such as those described in Japanese Patent Unexamined Publication (KOKAI) No.(Hei)7-97333/1996 may also be used.

<3> Method for Encapsulating Antigens by Using the Hydrophobized Polysaccharide

The complexes comprising the hydrophobized polysaccharide and the antigen can be isolated and purified by mixing microparticles of aggregated hydrophobized polysaccharide and antigens at room temperature, and then treating the mixture by gel chromatography (Nishikawa, Macromolecules, 27, pp.7654–7659, 1994). The resulting complexes of the hydrophobized polysaccharide and the antigen, per se, can be used as the vaccinal preparation of the present invention; however, they may optionally be subjected to further processes such as sterilization by standard methods.

<4> Immunization with the Complex Comprising the Hydrophobized Polysaccharide and the Antigen The vaccinal preparation of the present invention may be administered to an animal at a given amount for immunization in the same manner as other known vaccinal preparations, and the titer of the vaccinal preparation can also be determined similarly. The vaccinal preparation of the present invention is generally administered by subcutaneous injection. However, the routes of administration are not limited to the subcutaneous injection. For example, other parenteral administrations such as intravenous and intramuscular administrations, and oral administration can also be employed. Doses of the vaccinal preparation of the present invention to achieve immunization can be appropriately chosen. For example, a general dose may range from about 50 to 150 μg as the amount of an antigen per administration, and once to four administrations are preferred.

For the manufacture of the vaccinal preparation of the present invention as a pharmaceutical preparation, conventional excipients, carriers and diluents can be suitably used depending on the prescribed route of administration.

EXAMPLES

The present invention will be explained more specifically by referring to the following examples. However, the scope of the present invention is not limited to the following examples.

Example 1

Preparation of a Complex of Cholesterol-modified Mannan or Pullulan and Oncogene Product ErbB-2 Protein Hydrophobized polysaccharides were synthesized according to the method of Akiyoshi et al. (Akiyoshi et al., Macromolecules, 26, 3062–3068 (1993)). As a cholesterol-modified mannan, mannan having a molecular weight of about 55,000 (Sigma) modified with about 2.3 cholesterol residues per 100 monosaccharide units was obtained (abbreviated as "CHM-55-2.3" hereafter). As a cholesterol-modified pullulan, pullulan having a molecular weight of about 108,000 (Hayashibara Biochemistry Institute) modified with about 0.9 cholesterol residues per 100 monosaccharide was obtained (abbreviated as "CHP-108-0.9" hereafter). In aqueous solutions, each aggregate of the hydrophobized polysaccharides contained about 7 hydrophobic domains formed by 7 associated cholesterol residues in average.

The above-obtained hydrophobized polysaccharides were dissolved in DMSO, dialyzed against PBS (pH 7.9), and then sonicated by using a probe type sonicator (URP, Tomy Seiko) at 40W for 10 minutes. These solutions were filtered successively through membranes having a pore size of 1.2 μm, 0.45 μm, and 0.2 μm to obtain aqueous solutions of microparticles comprising aggregated hydrophobized polysaccharides. The concentration of the hydrophobized polysaccharide of each solution was determined as 9.62 mg/ml for CHP-108-0.9, and 6.97 mg/ml for CHM-55-2.3 by the phenol-sulfuric acid method.

A recombinant protein composed of a polypeptide corresponding to amino acids 1 to 147 of the oncogene product human ErbB-2 protein (Coussens et al., Science, 230, 1132, 1985), whose N-terminus was fused to a histidine hexamer, was expressed in *Escherichia coli* and used as antigen protein. A cDNA comprising a region encoding a polypeptide corresponding to the amino acids 1 to 147 of the human ErbB-2 protein was amplified by PCR using the following two oligonucleotide primers:

HN40: 5'-AGCTGCAGTGATCACCATGGAGCT-3'(SEQ ID NO:1 in SEQUENCE LISTING),and
HN51: 5'-TGAATTCTATGTGAGACTTCGAAGCTGCA-3'(SEQ ID NO:2 in SEQUENCE LISTING)

The resulting 463 bp DNA fragment was blunt-ended by T4 DNA polymerase treatment, and digested with a restriction endonuclease BclI. A plasmid expression vector, pQE11 (Qiagen), was digested with a restriction endonuclease HindIII, blunt-ended by using T4 DNA polymerase, and further digested with a restriction endonuclease BamHI. The resulting BamHI-ΔHindIII fragment of about 3.3 kbp derived from the pQE11 vector was ligated to the aforementioned PCR-amplified DNA fragment of the human ErbB-2 cDNA by using a ligation kit (Takara Shuzo), and used for the transformation of *E. coli* strain JM109. Restriction maps were prepared for ampicillin-resistant clones to chose correctly constructed clones. Then, according to the attached manual of Qiagen, a recombinant protein was purified. From the recombinant microorganisms cultured in 1 liter of a culture medium, about 20 mg of the recombinant protein was obtained.

A solution of the human ErbB-2 recombinant protein (containing 2.0 mg/ml of the protein in PBS/6M urea) was added to the aforementioned aqueous solution of hydrophobized polysaccharides and mixed to obtain a colorless and transparent solution containing the complex of the hydrophobized polysaccharides and the antigen (5 mg/ml of CHM or CHP, 0.25 mg/ml of the human ErbB-2 recombinant protein). As a result of DLS (Dynamic Light Scattering) measurement of the solution, it was found that complex microparticles having the particle size of about 250 nm and k2/k12 ratio of 0.156 was obtained (the resulting complex of the cholesterol-modified mannan and the ErbB-2 protein will be abbreviated as "CHM-erbB2", and the complex of the cholesterol-modified pullulan and the ErbB-2 protein as "CHP-erbB2").

On the other hand, under a condition where the same buffer was used but in the absence of the hydrophobized polysaccharides, all the human ErbB-2 recombinant protein was insolubilized and deposited as precipitates.

As a negative control for immunization experiments, a complex of each hydrophobized polysaccharide and a protein was prepared by using Carbonic Anhydrase II (Sigma, referred to as "CAB" hereinafter) (the complex of the cholesterol-modified mannan and CAB will be abbreviated as "CHM-CAB", and the complex of the cholesterol-modified pullulan and CAB as "CHP-CAB").

Example 2

Vaccinal Action of CHM-erbB2 and CHP-erbB2 (CTL-inducing Effect and Anticancer Effect)

A suspension of CHM-erbB2 or CHP-erbB2 prepared in Example 1 was subcutaneously administered twice with an interval of one week to female Balb/c mice, each group consisting of three mice, at the amount equivalent to 25 μg of the protein per mouse. Then, recombinant cells CMS7HE, which were prepared by expressing neo gene as a selection marker and human ErbB-2 in fibrosarcoma cell strain deriving from a mice syngeneic with Balb/c mice (see, DeLeo et al., J. Exp. Med., 146, 720, 1977) in a conventional manner, or recombinant cells CMS7neo, which were prepared by expressing only the neo gene derived from the mice fibrosarcoma cell line in a similar manner as a negative control, were subcutaneously inoculated to the mice.

Figure 1:
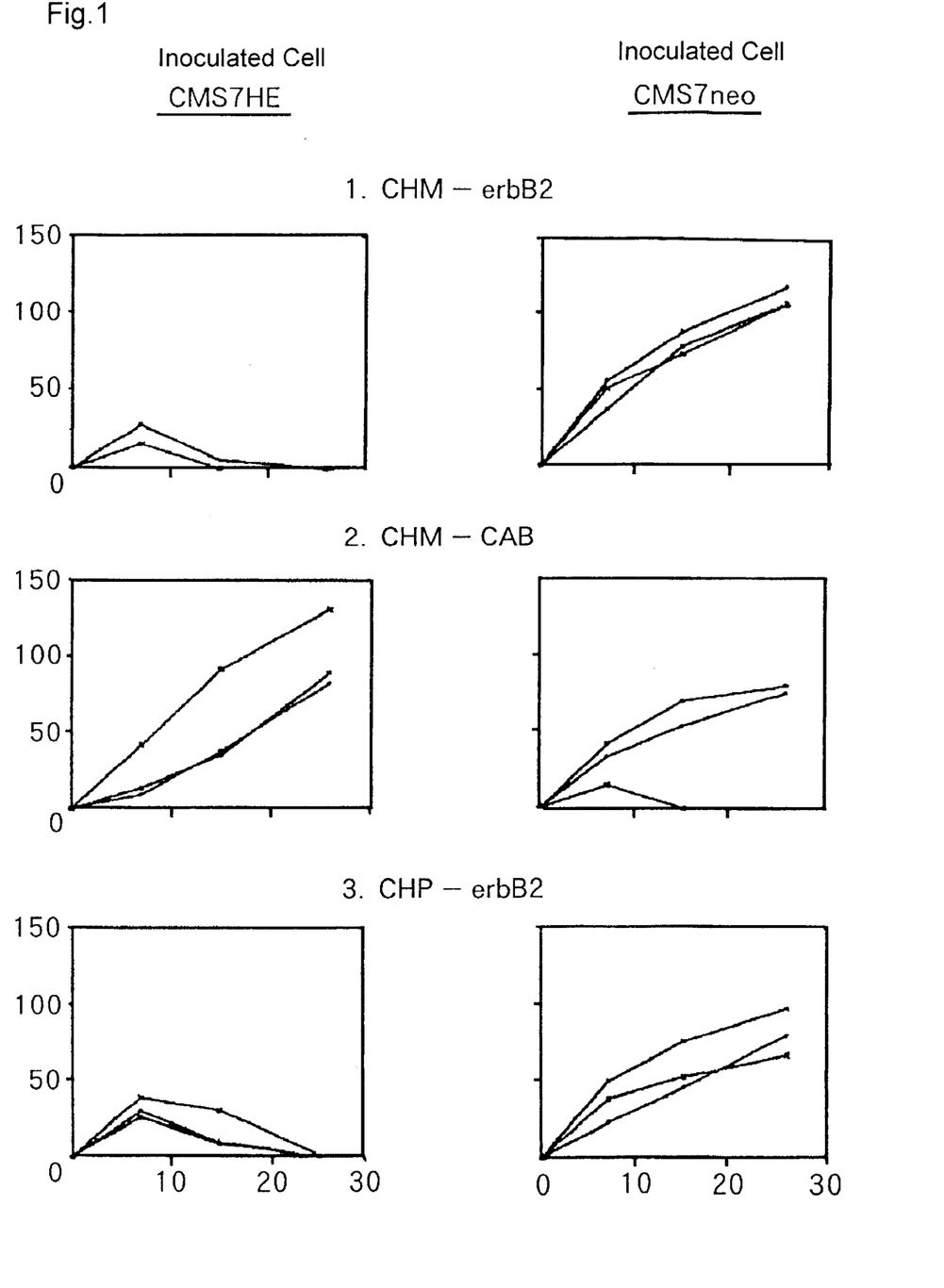
FIG. 1 depicts the growth curves of tumor cells on the mice immunized with preparations including a complex comprising cholesterol-modified mannan or cholesterol-modified pullulan and recombinant protein derived from human ErbB-2 oncogene then inoculated with human ErbB-2 expressing (CMS7HE) or non-expressing (CMS7neo) mouse cancer cells. The vertical axis represents the volume of the tumors (mm$^3$) calculated by approximate calculation using measured longitudinal and latitudinal length of the tumor, and the horizontal axis represents days after the tumor inoculation. In the figure, No. 1 to 3 show the data for the mice treated with CHM-erbB2, CHM-CAB (control group) and CHP-erbB2, respectively.
Figure 2:
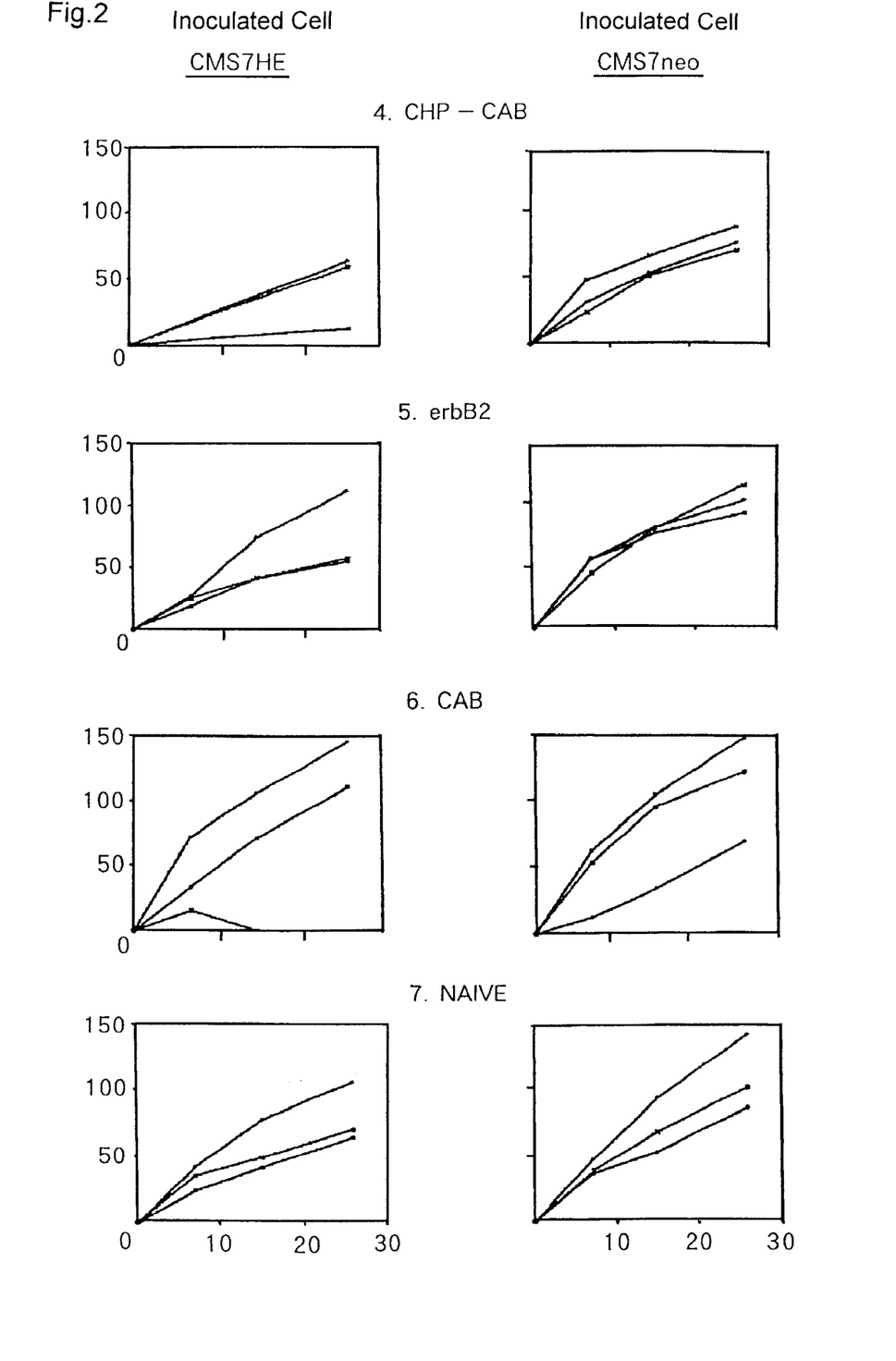
FIG. 2 depicts the growth curves of tumor cells on the mice immunized with preparations including a complex comprising cholesterol-modified mannan or cholesterol-modified pullulan and recombinant protein derived from human ErbB-2 oncogene then inoculated with human ErbB-2 expressing (CMS7HE) or non-expressing (CMS7neo) mouse cancer cells. The vertical axis represents the volume of the tumors (mm$^3$) calculated by approximate calculation using measured longitudinal and latitudinal length of the tumor, and the horizontal axis represents days after the tumor inoculation. In the figure, No. 4 to 7 show the data for the mice treated with CHP-CAB (control group), ErbB-2 protein only (control group), CAB only (control group) and non-immunized (naive) mice, respectively.

The size of the inoculated tumors was measured periodically. As shown in FIG. 1, the growth inhibition and complete regression of the tumor expressing human ErbB-2 was observed in all of the three mice immunized with CHM-erbB2 or CHP-erbB2 (FIG. 1, Nos. 1 and 3, left columns). On the other hand, as to the inoculated tumors not expressing the human ErbB-2, no inhibitory effect on the tumor growth was observed in the mice even when immunized with CHM-erbB2 or CHP-erbB2 (FIG. 1, Nos. 1 and 3, right columns), which suggested antigen-specificity of the immunization. As to the immunization with the recombinant human ErbB-2 (FIG. 2, No. 5) or with unrelated CAB (FIG. 1, No. 2 and FIG. 2, Nos. 4 and 6), elicited no tumor growth inhibitory effect.

Figure 3:
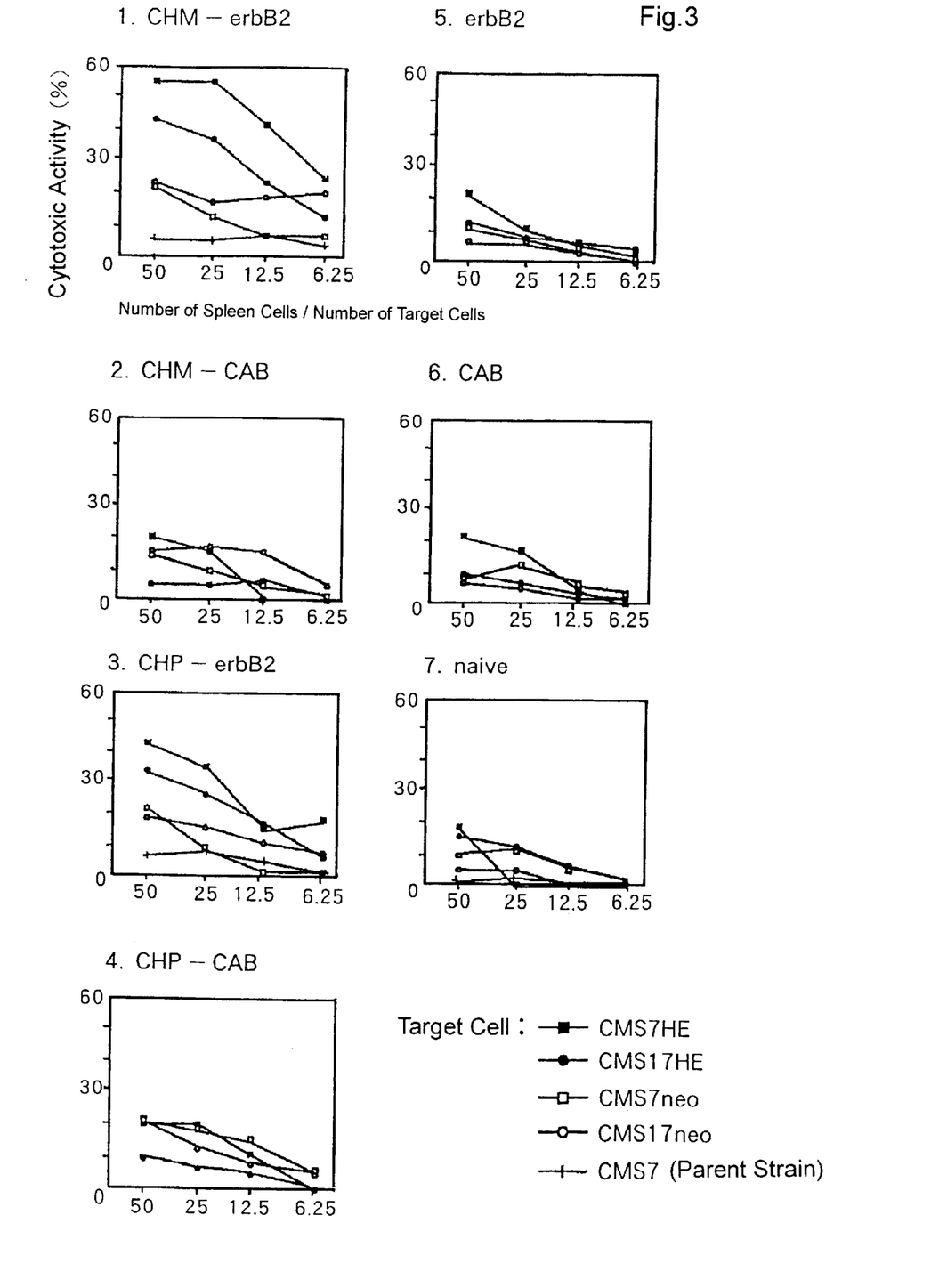
FIG. 3 shows the cytotoxic activity of the spleen cells collected from mice immunized under the same conditions as those in FIG. 1. The spleen cells were cultured in vitro with stimulated with human ErbB-2 expressing Balb/c mouse derived CMS17HE cells, and their cytotoxicity against $^{51}$Cr-labeled target cells was measured (the sequential numbers 1 to 7 in FIG. 3 corresponds to the numbers of the immunization group defined in FIGS. 1 and 2). In the figure, the vertical axis represents cytotoxicity calculated by subtracting the fraction of the non-specific leak of $^{51}$Cr from the labeled cells, and the horizontal axis represents the ratio of the number of the spleen cells to that of the target cells.

Spleen cells were collected from the mice immunized in the same manner as described above, and stimulated with CMS17HE cells which was syngeneic with Balb/c mice and expressing human ErbB-2, which had been treated by radiation in vitro, and their cytotoxicity against $^{51}$Cr-labeled CMS7HE cells, CMS17HE cells, CMS7neo cells, CMS17neo cells and CMS7 cells was measured in a standard method. As shown in FIG. 3, only when the spleen cells obtained from the mice immunized with CHM-erbB2 or CHP-erbB2 were used, the human ErbB-2 expressing cells (CMS7HE; CMS17HE cells were used as a positive control because the cells were used for the stimulation) were remarkably damaged or killed depending on the ratio of the target cell number and the spleen cell number, compared to the non-expressing cells (CMS7neo, CMS17neo and CMS7) (FIG. 3, Nos. 1 and 3).

Figure 4:
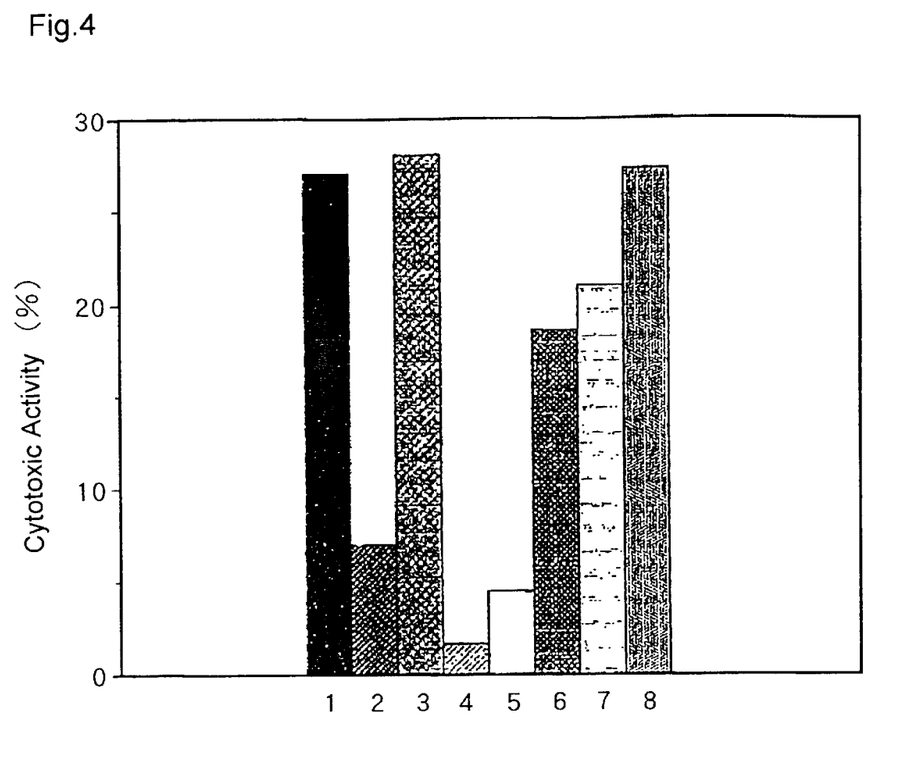
FIG. 4 depicts the differences of human ErbB-2 specific CTL activities when monoclonal antibodies recognizing various mouse immunocyte-surface markers were added at a concentration of 1:2 dilution ratio under the same conditions as the CHM-erbB2 immunized group in FIG. 3. In the figure, No. 1 represents the data obtained in the absence of any antibodies, No. 2 in the presence of anti-CD3 antibody, No. 3 in the presence of anti-CD4 antibody, No. 4 in the presence of anti-CD8 antibody, No. 5 in the presence of anti-Kd antibody, No. 6 in the presence of anti-Dd antibody, No. 7 in the presence of anti-Ld antibody, and No. 8 in the presence of anti-MHC class II antibody.

In the above experiments, when monoclonal antibodies for various mouse lymphocyte surface markers were added at a concentration of 1:2 dilution during the course of the assay for the human ErbB-2 specific CTL activity of the spleen cells obtained from CHM-erbB2 immunized mice, only the antibodies against Kd inhibited human ErbB-2 specific CTL activity among those against CD3, CD8, and mouse MHC class I molecule (FIG. 4). anti-CD4, anti-Dd, anti-Ld or anti-mouse MHC class II molecule antibodies did not exhibit such activity. These results suggest that the observed human ErbB-2 specific CTL activity was elicited by MHC class I-restricted CD8 positive T lymphocytes.

INDUSTRIAL APPLICABILITY

The vaccinal preparation of the present invention has excellent modifying effects on immune response to antigens, in particular, activation or induction of cytotoxic T cells, and can be used as a vaccine for preventive and/or therapeutic treatment of cancers, viral diseases, and autoimmune diseases.

What is claimed is:

1. A parenteral vaccinal preparation comprising hydrophobized polysaccharide and antigen, wherein the hydrophobized polysaccharide comprises from about 0.9 to about 5 hydrophobic groups per 100 monosaccharide units and wherein the antigen is selected from tumor-associated antigens, viral antigens and autoantigen-reactive T-cell receptors.

2. The vaccinal preparation of claim 1, wherein the hydrophobic groups are selected from alkyl groups and sterol residues.

3. The vaccinal preparation of claim 2, wherein the sterol residues comprise a cholesterol residue.

4. The vaccinal preparation of claim 1, wherein the hydrophobized polysaccharide comprises saccharide units whose primary hydroxyl group is represented by the following formula:

wherein R represents an alkyl group or a sterol residue; m represents 0 or 1; and n represents a positive integer.

5. The vaccinal preparation of claim 1, wherein the antigen is selected from antigenic proteins having a molecular weight of about 2,000 to about 100,000.

6. The vaccinal preparation of claim 5, wherein the antigen is capable of at least one of activation and induction of cytotoxic T-cells.

7. The vaccinal preparation of claim 1, wherein the preparation is free of phospholipids.

8. The vaccinal preparation of claim 1, further comprising at least one of an excipient, a carrier and a diluent suitable for parenteral administration.

9. A parenteral vaccinal preparation comprising hydrophobized polysaccharide and antigen, wherein the hydrophobized polysaccharide comprises hydrophobic groups in a ratio of modifications to molecule of about 5% by weight or less and wherein the antigen is selected from tumor-associated antigens, viral antigens and autoantigen-reactive T-cell receptors.

10. The vaccinal preparation of claim 9, wherein the antigen is encapsulated by microparticles of aggregated hydrophobized polysaccharide.

11. The vaccinal preparation of claim 9, wherein the polysaccharide is selected from pullulan and mannan.

12. A microparticle for use in a vaccinal preparation, the microparticle consisting essentially of hydrophobized polysaccharide and antigen selected from tumor-associated antigens, viral antigens and autoantigen-reactive T-cell receptors.

13. The microparticle of claim 12, wherein the hydrophobized polysaccharide is aggregated.

14. The microparticle of claim 13, wherein the aggregated hydrophobized polysaccharide encapsulates said antigen.

15. The microparticle of claim 13, wherein the hydrophobized polysaccharide comprises from about 0.9 to about 5 hydrophobic groups per 100 monosaccharide units.

16. A parenteral vaccinal preparation comprising an antigen and an adjuvant, wherein the adjuvant comprises a hydrophobized polysaccharide having from about 0.9 to about 5 hydrophobic groups per 100 monosaccharide units and wherein the antigen is selected from tumor-associated antigens, viral antigens and autoantigen-reactive T-cell receptors.

17. The vaccinal preparation of claim 16, wherein the polysaccharide is selected from mannan and pullulan.

18. A method of immunization which comprises parenterally administering to a mammal a vaccinal preparation comprising hydrophobized polysaccharide and antigen.

19. The method of claim 18, wherein the antigen is capable of at least one of induction and activation of cytotoxic T-cells.

20. The method of claim 19, wherein the cytotoxic T-cell is antigen-specific.

21. The method of claim 18, wherein the hydrophobized polysaccharide comprises from about 0.9 to about 5 hydrophobic groups per 100 monosaccharide units.

22. The method of claim 18, wherein the hydrophobic groups are selected from alkyl groups and sterol residues.

23. The method of claim 22, wherein the sterol residues comprise a cholesterol residue.

24. The method of claim 18, wherein the antigen is selected from antigenic proteins having a molecular weight of from about 2,000 to about 100,000.

25. The method of claim 18, wherein the antigen comprises erbB-2 protein.

26. The method of claim 18, wherein the amount of antigen per administration is from about 50 to about 150 μg.

27. The method of claim 26, comprising from about one to about four administrations.

28. The method of claim 27, wherein the administration is subcutaneous.

29. A method of preventing a condition selected from a viral disease and an autoimmune disease, in a mammal, wherein the method comprises parenterally administering to said mammal a pharmaceutical preparation comprising hydrophobized polysaccharide and antigen.

30. A method of treating a condition selected from cancer, a viral disease and an autoimmune disease, in a mammal in need of such treatment, wherein the method comprises parenterally administering to said mammal an effective amount of a vaccinal preparation comprising hydrophobized polysaccharide and antigen.

31. The method of claim 30 wherein the condition is cancer.

32. A process for making a vaccinal preparation comprising a hydrophobized polysaccharide and an antigen, the process comprising mixing microparticles of aggregated hydrophobized polysaccharide and antigen and subjecting the resultant mixture to gel chromatography.

33. The process of claim 32, wherein said microparticles are made by a process comprising sonicating a solution of hydrophobized polysaccharide and filtering the sonicated solution through at least one membrane.

34. A vaccinal preparation comprising hydrophobized polysaccharide and antigen, wherein the hydrophobized polysaccharide comprises from about 0.9 to about 5 hydrophobic groups per 100 monosaccharide units and wherein the antigen is selected from tumor-associated antigens.

35. The vaccinal preparation of claim 34, wherein the hydrophobic groups are selected from alkyl groups and sterol residues.

36. The vaccinal preparation of claim 35, wherein the sterol residues comprise a cholesterol residue.

37. The vaccinal preparation of claim 34, wherein the hydrophobized polysaccharide comprises saccharide units whose primary hydroxyl group is represented by the following formula:

—O—(CH$_2$)$_m$CONH(CH$_2$)$_n$NH—CO—O—R wherein R represents an alkyl group or a sterol residue; m represents 0 or 1; and n represents a positive integer.

38. The vaccinal preparation of claim 37, wherein the polysaccharide is selected from pullulan and mannan.

39. A process for making a pharmaceutical composition comprising at least one active ingredient, comprising combining the at least one active ingredient with an adjuvant, wherein the adjuvant comprises a hydrophobized polysaccharide having from about 0.9 to about 5 hydrophobic groups per 100 monosaccharide units.

40. The process of claim 39, wherein the hydrophobic groups are selected from alkyl groups and sterol residues.

41. The process of claim 39, wherein the hydrophobized polysaccharide comprises saccharide units whose primary hydroxyl group is represented by the following formula:

—O—(CH$_2$)$_m$CONH(CH$_2$)$_n$NH—CO—O—R wherein R represents an alkyl group or a sterol residue; m represents 0 or 1; and n represents a positive integer.

42. A vaccinal preparation comprising hydrophobized polysaccharide and antigen, wherein the hydrophobized polysaccharide is selected from (a) mannan having a molecular weight of about 55,000 and being modified with about 2.3 cholesterol residues per 100 monosaccharide units and (b) pullulan having a molecular weight of about 108,000 and being modified with about 0.9 cholesterol residues per 100 monosaccharide units and wherein the antigen is erbB-2 protein.

43. The vaccinal preparation of claim 42, wherein the vaccinal preparation is a parenteral vaccinal preparation.

44. The vaccinal preparation of claim 43, further comprising at least one of an excipient, a carrier and a diluent suitable for parenteral administration.

45. The vaccinal preparation of claim 42, wherein the preparation is free of phospholipids.

46. A complex comprising erbB-2 protein and a hydrophobized polysaccharide selected from (a) mannan having a molecular weight of about 55,000 and being modified with about 2.3 cholesterol residues per 100 monosaccharide units and (b) pullulan having a molecular weight of about 108,000 and being modified with about 0.9 cholesterol residues per 100 monosaccharide units.

47. A microparticle for use in a vaccinal preparation, the microparticle comprising erbB-2 protein and a hydrophobized polysaccharide selected from (a) mannan having a molecular weight of about 55,000 and being modified with about 2.3 cholesterol residues per 100 monosaccharide units and (b) pullulan having a molecular weight of about 108,000 and being modified with about 0.9 cholesterol residues per 100 monosaccharide units.

48. A method of immunization which comprises parenterally administering to a mammal a vaccinal preparation comprising erbB-2 protein and a hydrophobized polysaccharide selected from (a) mannan having a molecular weight of about 55,000 and being modified with about 2.3 cholesterol residues per 100 monosaccharide units and (b) pullulan having a molecular weight of about 108,000 and being modified with about 0.9 cholesterol residues per 100 monosaccharide units.

49. The method of claim 48, wherein the amount of erbB-2 protein per administration is from about 50 to about 150 µg.

50. The method of claim 49, comprising from about one to about four administrations.

51. The method of claim 48, wherein the administration is subcutaneous.

52. A method of inducing cytotoxic T-cells which comprises administering to a mammal a vaccinal preparation comprising erbB-2 protein and a hydrophobized polysaccharide selected from (a) mannan having a molecular weight of about 55,000 and being modified with about 2.3 cholesterol residues per 100 monosaccharide units and (b) pullulan having a molecular weight of about 108,000 and being modified with about 0.9 cholesterol residues per 100 monosaccharide units.

53. A method of activating cytotoxic T-cells which comprises administering to a mammal a vaccinal preparation comprising erbB-2 protein and a hydrophobized polysaccharide selected from (a) mannan having a molecular weight of about 55,000 and being modified with about 2.3 cholesterol residues per 100 monosaccharide units and (b) pullulan having a molecular weight of about 108,000 and being modified with about 0.9 cholesterol residues per 100 monosaccharide units.

54. A method of treating cancer in a mammal in need of such treatment, wherein the method comprises parenterally administering to said mammal a therapeutically effective amount of a vaccinal preparation comprising erbB-2 protein and a hydrophobized polysaccharide selected from (a) mannan having a molecular weight of about 55,000 and being modified with about 2.3 cholesterol residues per 100 monosaccharide units and (b) pullulan having a molecular weight of about 108,000 and being modified with about 0.9 cholesterol residues per 100 monosaccharide units.

55. A process for making a vaccinal preparation, the process comprising mixing microparticles of erbB-2 protein and aggregated hydrophobized polysaccharide selected from (a) mannan having a molecular weight of about 55,000 and being modified with about 2.3 cholesterol residues per 100 monosaccharide units and (b) pullulan having a molecular weight of about 108,000 and being modified with about 0.9 cholesterol residues per 100 monosaccharide units, and subjecting the resultant mixture to gel chromatography.

56. The process of claim 55, wherein said microparticles are made by a process comprising sonicating a solution of hydrophobized polysaccharide and filtering the sonicated solution through at least one membrane.

* * * * *

UNITED STATES PATENT AND TRADEMARK OFFICE
CERTIFICATE OF CORRECTION

PATENT NO. : 6,656,481 B1
DATED : December 2, 2003
INVENTOR(S) : H. Shiku et al.

It is certified that error appears in the above-identified patent and that said Letters Patent is hereby corrected as shown below:

Column 11,
Line 1, "claim 27" should be -- claim 18 --.

Signed and Sealed this

Second Day of August, 2005

JON W. DUDAS
*Director of the United States Patent and Trademark Office*